US006990868B2

(12) United States Patent
Hardcastle, III (10) Patent No.: US 6,990,868 B2
(45) Date of Patent: Jan. 31, 2006

(54) ACCELERATED WEATHERING APPARATUS HAVING SEALED WEATHERING CHAMBER

(75) Inventor: Henry K. Hardcastle, III, Sunrise, FL (US)

(73) Assignee: Atlas Material Testing Techology LLC, Chicago, IL (US)

( * ) Notice: Subject to any disclaimer, the term of this patent is extended or adjusted under 35 U.S.C. 154(b) by 440 days.

(21) Appl. No.: 10/295,098

(22) Filed: Nov. 15, 2002

(65) Prior Publication Data

US 2004/0093965 A1 May 20, 2004

(51) Int. Cl.
G01N 3/02 (2006.01)
G01N 25/72 (2006.01)
G01N 3/60 (2006.01)
G01N 17/00 (2006.01)

(52) U.S. Cl. .............................. 73/856.6; 374/5; 374/57
(58) Field of Classification Search .................... 374/5, 374/33, 57; 73/865.6
See application file for complete search history.

(56) References Cited

U.S. PATENT DOCUMENTS

| | | | |
|---|---|---|---|
| 2,945,417 A * | 7/1960 | Caryl et al. .................. | 126/600 |
| 3,340,397 A | 9/1967 | Johnston ..................... | 378/195 |
| 3,664,188 A | 5/1972 | Kockott ..................... | 73/150 R |
| 3,889,531 A * | 6/1975 | Suga ......................... | 73/150 R |
| 4,012,954 A | 3/1977 | Klippert .................... | 73/150 R |
| 4,602,503 A | 7/1986 | Hile et al. ................. | 73/865.6 |
| 4,698,507 A | 10/1987 | Tator et al. ................ | 250/429 |
| 4,770,031 A | 9/1988 | Roth et al. .................... | 73/147 |
| 4,807,247 A * | 2/1989 | Robbins, III ................ | 374/57 |
| 4,825,078 A | 4/1989 | Huber et al. ................ | 250/372 |
| 4,874,952 A | 10/1989 | Arnaud et al. ......... | 250/455.11 |
| 4,975,047 A | 12/1990 | Mitsuhashi et al. ........... | 432/23 |
| 5,281,535 A | 1/1994 | Wei et al. ...................... | 436/6 |
| 5,818,599 A | 10/1998 | Plavnik et al. .............. | 356/440 |
| 6,073,500 A | 6/2000 | Jorgensen et al. ......... | 73/865.6 |

* cited by examiner

Primary Examiner—Hezron Williams
Assistant Examiner—Tamiko Bellamy
(74) Attorney, Agent, or Firm—Vedder Price Kaufman & Kammholz (57) ABSTRACT

An accelerated weathering apparatus of the type used to concentrate solar radiation upon test specimens includes a frame supporting a reflecting solar concentrator disposed in opposition to a target board. A channel is connected to the target board and includes a cover to define a chamber. A fluid source is in communication with the chamber, whereby a fluid introduced into the chamber reacts with the test specimens in order to accelerate degradation of the test specimens during exposure to concentrated solar radiation. Cooling apparatus contiguous with the test specimens may also be included.

83 Claims, 10 Drawing Sheets

ACCELERATED WEATHERING APPARATUS HAVING SEALED WEATHERING CHAMBER

FIELD OF THE INVENTION

The present invention relates generally to an accelerated weathering apparatus of the type used to expose test specimens to solar radiation and other weathering effects on an accelerated basis, and more particularly, to an improved accelerated weathering apparatus that provides a sealed weathering chamber to increase the rate of accelerated weathering degradation of the test specimen. In one embodiment of the present invention, oxygen is introduced into the sealed weathering chamber in order to increase the diffusion of oxygen into the test specimens and when combined with increased levels of ultraviolet light thereby increase photo-oxidation. Other embodiments of this invention introduce other fluids in order to provide the desired weathering effect.

BACKGROUND OF THE INVENTION

Manufacturers of exterior coatings, such as paints and other finishes, as well as plastics and other components which tend to degrade under exposure to solar radiation and other weathering effects, want to know how such products will perform following years of exposure. However, such manufacturers typically require this information in a much shorter time period than it would take to expose such materials to weathering effects under normal conditions. Accordingly, accelerated weathering apparatus have been developed which accelerate the effects of weathering due to outdoor exposure in a much shorter time so that manufacturers need not actually wait five or ten years in order to determine how their products will hold up after five or ten years of actual outdoor exposure.

Weathering is the adverse response of a material or product to its climate, often causing unwanted and premature product failures. Consumers spend millions of dollars per year to maintain products that inevitably degrade and to replace products that fail. Materials that fail as a result of exposure to outdoor environments account for a significant portion of this total cost.

The three main factors of weathering are solar radiation (light energy), temperature and water (moisture). But it is not just "how much" of each of these factors ultimately cause degradation to materials, because different types of solar radiation, different phases of moisture, and temperature cycling have a significant effect on materials on exposure. These factors, in conjunction with secondary effects such as airborne pollutants, biological phenomenon, and acid rain, act together to cause "weathering."

One outdoor natural accelerated weathering test apparatus ("ONAWTA") is disclosed in U.S. Pat. No. 4,807,247, issued to Robbins, III.

A specimen that is undergoing an outdoor accelerated weathering exposure test experiences high levels of natural ultraviolet irradiation and is expected to provide an accelerated indication of how the test specimen material will degrade under natural exposure to ultraviolet weathering. Photo-oxidation weathering reactions require oxygen. Surface layers of the test specimen material readily absorb oxygen from adjacent ambient air volume. However, important weathering reactions may also take place in the bulk or "non-surface areas" of thicker volumes of test specimen material. At lower ultraviolet intensities, as observed in natural or un-accelerated weathering, the rate of oxygen use in bulk photo-oxidation weathering reactions may achieve a balance with the rate of diffusion of oxygen from the ambient air volume into the bulk volume of test specimen material.

Accelerated weathering test apparatus, however, may produce very high UV intensities. As a result, oxygen diffusion from ambient air volume may not occur at a rate fast enough to supply oxygen for photo-oxidation reaction rates may not increase even when the UV intensity is increased many times, since the oxygen concentration in the bulk may be limited by diffusion.

ONATW As, however, produce very high ultraviolet intensities. As a result, oxygen diffusion from the ambient air volume may not occur at a rate fast enough to supply oxygen for photo-oxidation reactions in the bulk of test specimen materials. Consequently, bulk photo-oxidation reaction rates may not increase even when the ultraviolet intensity is increased many times, since the oxygen concentration in the bulk is limited by diffusion rates.

A conventional indoor artificial accelerated weathering test apparatus ("IAAWTA") which exposes test specimens to selected atmospheres at superambient pressures is disclosed in U.S. Pat. No. 3,664,188, issued to Kockott. This reference includes a test container which is radiation permeable, yet sealed for filling with a suitable atmosphere at a selected pressure. Kockott asserts that the small test container which holds a test speciment is easier to seal. Thus, the atmosphere the specimens are exposed to may be more easily controlled. Alternatively, in apparatus prior to Kockott, the whole test chamber, including the radiation source and all the specimen carriers, is sealed to permit introduction of special atmospheres.

There are several disadvantages of the outdoor natural and indoor artificial accelerated weathering test apparatus discussed above. One disadvantage is that no prior art ONAWTA, such as Robbins, disclose or teach the concept of increasing the presence and/or pressure of oxygen or other fluids other than water around the test specimens. The old testing method simply exposed the test specimens to high ultraviolet exposure under ambient conditions of oxygen. Accordingly, the diffusion rate of oxygen into the test specimen under ambient conditions was limited. Therefore, no matter how accelerated the dose of ultraviolet irradiation, the degradation rate was limited by the diffusion rate of oxygen into the material at ambient concentrations of oxygen in the ambient atmosphere surrounding the test specimen.

Further, the IAAWTA does not teach, suggest or provide motivation to use the inventions disclosed therein in connection with a ONAWTA. One reason such teaching or suggestion is absent is that such IAAWTA fail to duplicate the actual light spectrum of natural sunlight to which the test specimens will actually be exposed to in everyday use and the intensity of natural accelerated weathering apparatus.

It has been acknowledged and recognized by those of skill in the art that the outdoor natural solar light source and indoor artificial light source test apparatus are distinct from one another and provide different sets of empirical data. For example, the Society of Automotive Engineers ("SAE") has issued Standard Test Method J1961 for accelerated exposure of automotive exterior materials using a solar fresnel-reflective apparatus (outdoor natural solar light source) and Standard Test Method J1960 for accelerated exposure of automotive exterior materials using a controlled irradiance water-cooled Xenon arc apparatus (indoor, artificial light source).

Yet another disadvantage of the INAAWTA is that the spectral power distribution of the ONAWTA is difficult to reproduce. The intensity of the IAAWTA can be adjusted by increasing power. However, the spectral power distribution is substantially different than the sun. Thus, the wavelengths present from the INAAWTA are magnified by the increase in power. As a result, the unnatural degradation mechanisms associated with such wavelengths are also magnified. Therefore, the ONAWTA often provides a more realistic set of data results than the artificial accelerated weathering apparatus because of the closer match to the solar spectrum power distribution found in a test specimen's end use environment.

Therefore, there exists a need in the art for an improved natural accelerated weathering apparatus having a sealed weathering chamber for providing increased rates of photo-oxidation and cooling for the test specimen.

DETAILED DESCRIPTION OF A PREFERRED EMBODIMENT OF THE INVENTION

Briefly, in one embodiment, the accelerated weathering apparatus of the type used to concentrate solar radiation upon test specimens includes a frame supporting a reflecting solar concentrator disposed in opposition to a target board. A channel is connected to the target board and includes a cover to define a chamber. A fluid source is in communication with the chamber, whereby a fluid introduced into the chamber reacts with the test specimens, in order to accelerate degradation of the test specimens during exposure to concentrated solar radiation.

In another embodiment, the accelerated weathering apparatus of the type used to concentrate solar radiation upon test specimens includes a frame supporting a reflecting solar concentrator disposed in opposition to an air tunnel having a fan for moving air therethrough and a target board. A channel is connected to the target board and includes a cover to define a chamber. A test specimen is disposed within the chamber. An apparatus is contiguous with the specimen for maintaining the specimen at a desired temperature.

In yet another embodiment, an accelerated weathering apparatus of the type used to concentrate solar radiation upon test specimens includes a frame for supporting a reflecting solar concentrated disposed in opposition to a target board. A channel is connected to the target board and includes a cover to define a chamber. A specimen is disposed within the chamber to define a cavity such that a first side of the specimen is exposed to the chamber and a second side of the specimen is exposed to the cavity. An apparatus is disposed within the cavity contiguous with the specimen for maintaining the specimen at a desired temperature.

Figure 1:
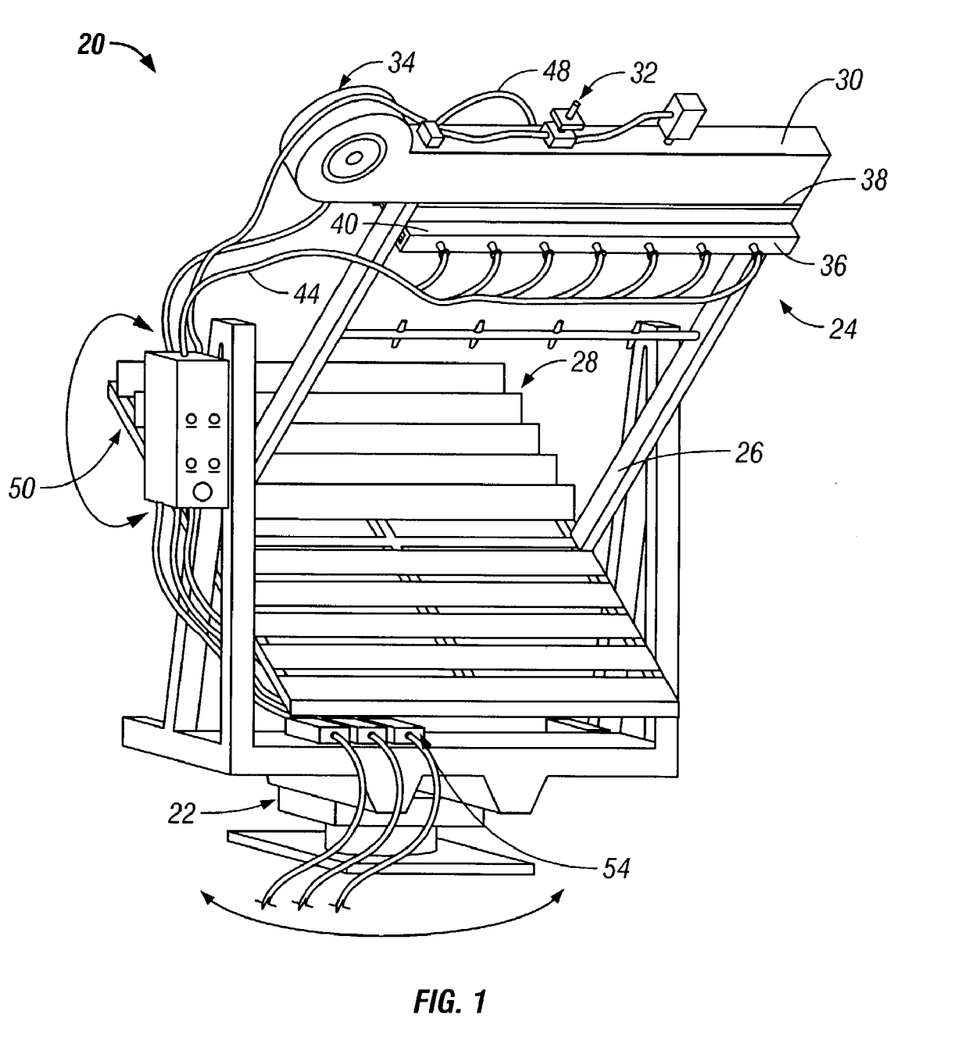
FIG. 1 is a perspective view of an ONAWTA in accordance with one embodiment of the invention.

FIG. 1 shows a perspective view of an ONAWTA in accordance with an embodiment of the present invention designated generally by reference numeral 20. The accelerated weathering apparatus 20 concentrates solar radiation upon a plurality of test specimens and exposes such tests specimens to a fluid from a fluid source during a test cycle. It will be recognized by those of skill in the art that the fluid may take the form of a liquid, gas or combination of liquid and gas. The basic accelerated weathering apparatus 20 includes a support member 22 connected to an operative portion 24. The operative portion 24 includes a frame 26 which supports a reflecting solar concentrator 28 disposed in opposition to an air tunnel 30.

Figure 2:
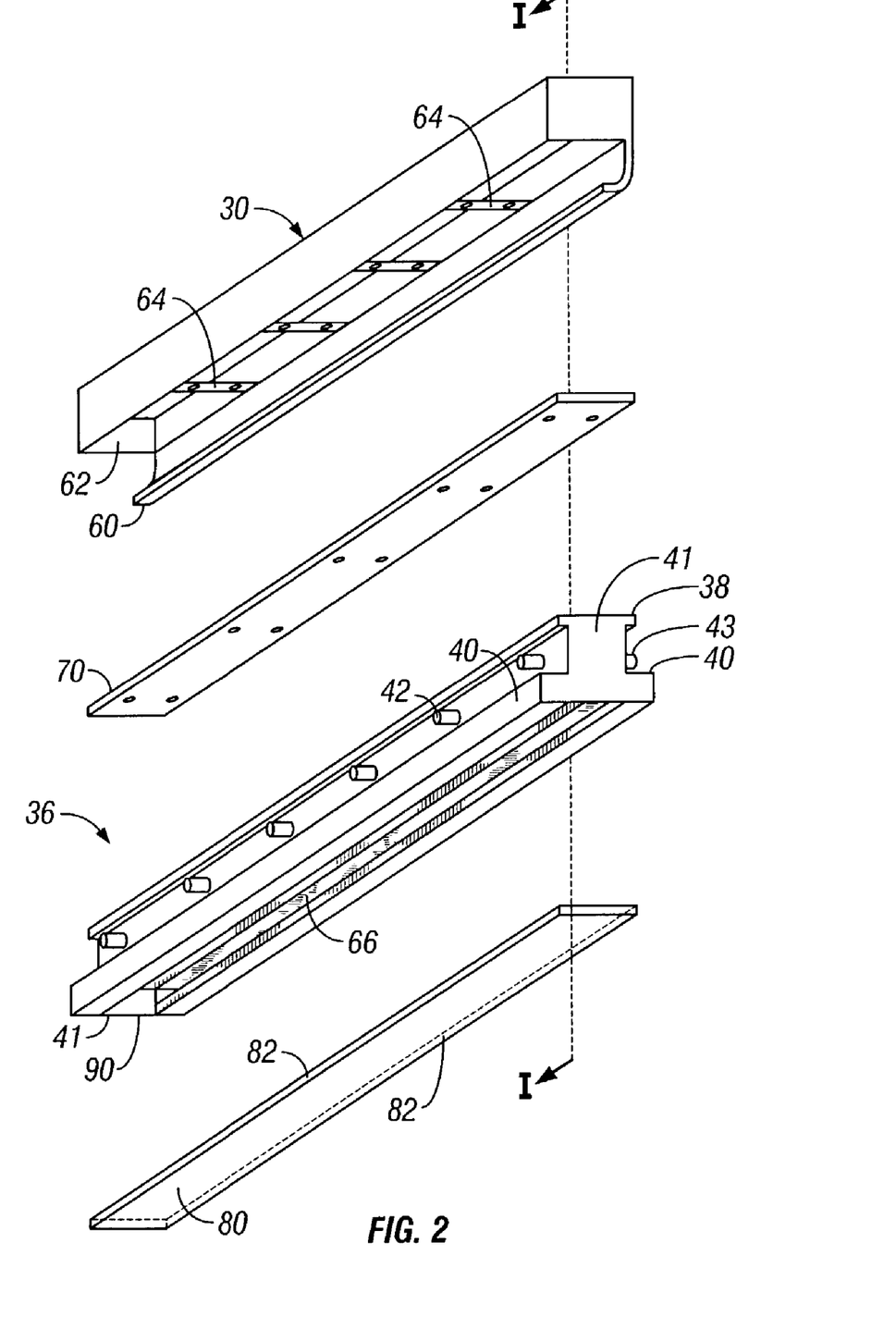
FIG. 2 is an exploded view of a portion of the ONAWTA of FIG. 1.

The reflecting solar concentrator 28 is configured as a fresnel-reflecting apparatus having a series of ten flat mirrors which focus natural sunlight onto a series of test specimens secured to a target board (as best shown in FIG. 2) secured to the air tunnel 30 which measures approximately six (6) inches wide by fifty-five (55) inches long. The fresnel-reflecting solar concentrator directs solar radiation onto the target board area with an intensity of approximately eight suns. It will be recognized by those of skill in the art that the intensity of the concentrator may be increased or decreased by adding or subtracting mirrors, changing the reflectance characteristics of the mirrors, inserting filtering elements in the optical path between the mirrors and the test specimens or in any other suitable manner Both the mirror bed of the solar concentrator 28 and the target board are supported by a frame 26 which can be rotated to follow daily movements of the sun. A solar tracking mechanism 32 responsive to the position of the sun controls the operation of an electric motor used to rotate the test apparatus to follow movements of the sun. The solar tracking mechanism 32 may be any conventionally available apparatus which provides such function.

Standardized testing methods have been developed for operating outdoor accelerated weathering test apparatus of the type described herein. The American Society for Testing Materials (ASTM) has issued standards such as, but not limited to, Standard G90 which is directed to testing procedures and operating parameters for targeting such outdoor accelerated weathering tests. Other standards have been developed by SAE (as briefly discussed above), Ford, International Standards Organization (ISO), American National Standards Institute (ANSI), Japan Industrial Standard (JIS) and other such standards organizations which are directed to accelerated weathering tests. However, no standard has been developed which incorporates use of a sealed weathering chamber in connection with an ONAWTA test cycle.

The support member 22 may be formed as a dual-access tracking apparatus as shown in FIG. 1 or as a single-axis tracking apparatus as shown in Robbins, III, discussed above. Both tracking apparatus may use any conventional solar tracking unit 32 which controls the orientation and position of the support member 22 and operative portion 24 in order to maintain the mirror bed 28 perpendicular to incident rays of sunlight. Both of these support members are well-known in the art and described in ASTM Standard G90-94. It is within the teachings of the present invention that other suitable support members could be utilized for providing adjustment of the apparatus relative to the sun.

The frame 26 extends upwardly and perpendicular to the mirror bed 28. The air tunnel 30 has a generally rectangular cross-section and is supported by the upper ends of the frame 26. An air circulation mechanism 34, preferably in the form of a squirrel cage blower assembly, is in communication with one end of the tunnel 30. It will be recognized that any apparatus suitable for moving air may be substituted for the squirrel cage blower. The squirrel cage blower assembly preferably includes a fan driven by an electric motor to circulate cooling ambient air through the tunnel 30. It is within the teachings of the present invention that any conventional control system may be associated with the air circulation mechanism 34. For example, the control system may include temperature sensing panels associated with sensors to determine the temperature of the test specimens on the target board in order to selectively control the application of electrical power to the electrical motor within the squirrel cage blower assembly or any other suitable control system.

The air tunnel 30 includes a deflector (as best shown in FIG. 2) which extends for the length of the target board and, in a conventional application, as taught in Robbins, III, causes cooling ambient air to be circulated in the direction across the target board for cooling test specimens. As will be discussed below, the air deflector serves a different function in the present invention and acts primarily as a vent to direct cooling air from the air tunnel.

In this embodiment of the present invention, a channel 36 is connected to the target board and includes a cover (as best shown in FIG. 2) to define a chamber. A fluid source (as described in detail below) is in communication with the chamber whereby fluid is introduced into the chamber in order to react with a specimen in order to accelerate degradation of the specimen during and between periods of exposure to concentrated solar radiation. The channel 36 includes a base 38 and a pair of oppositely disposed, elongated sidewalls 40 extending from the base. At least one first port 42 is disposed in one of the sidewalls 40. A first conduit 44 operatively connects each first port 42 to the fluid source such that the first conduit in each first port defines a first passageway for the fluid from the fluid source to the chamber.

A control apparatus 50 is preferably available and programmable to control, among other things related to the general operation of the accelerated weathering apparatus 20 (i.e. solar tracking and minor bed adjustments), at least one regulator operatively connected to the first passageway, the fluid source for controlling the supply of the fluid from the fluid source to the chamber and at least one second regulator 54 operatively connected to a second passageway for controlling the desired rate of removing the fluid from the chamber. Each of the at least one first and second regulators is responsive to the control apparatus 50 such that a signal from the control apparatus 50 actuates the regulator from a first normally closed position to a second open position for a desired period of time so that fluid may be supplied to or removed from the chamber during a test cycle. It is within the teachings of this invention that each of the at least one first and second regulators may be opened from the first normally closed to a second open position which is some desired percentage of the full open position. It will be recognized that the control apparatus 50 is preferably of an electrical/electronic design which is programmable to provide the above functions and that a mechanical design can be utilized to provide identical functionality. For example, while a digital solid state apparatus is preferred for simplicity, programmability, reliability and cost, it will be recognized that an analog apparatus, such as a timer-based system will provide the same function. Further, it is also within the teachings of this invention that activation of the regulators can also be performed manually by an operator.

FIG. 2 is an exploded view of a portion of one embodiment the accelerated weathering apparatus of the present invention. The air tunnel 30 is shown in an inverted position so that the bottom of such tunnel and the air deflector 60 are clearly shown. An open side 62 is defined in the air tunnel 30 and the target board 70 is connected thereto. A plurality of support struts 64 extend from one elongated side of the air tunnel 30 to the other across the open side 62 in order to connect the target board 70.

Preferably, the target board 70 is connected to the support struts 64 by means of a threaded fastener extending through the apertures in the support struts 64 and the target board 70. It will be recognized by those in the skill of the art that other forms of connection may be used to connect the target board 70 to the air tunnel 30. For example, quarter-turn fasteners, hook and loop fasteners, push fit fasteners, adhesives or any other suitable fastener apparatus may be used to removably connect the target board 70 to the air tunnel 30.

The target board 70 has a width dimension which is less than the width dimension of the open side 62 in order to define a gap through which air generated by the air circulation mechanism is channeled to the air deflector 60 for routing across the specimens, conventionally mounted to the target board 70. However, in the present invention, a channel 36 is connected to the target board 70 and the test specimens are mounted therein. Therefore, the gap provides a discharge for cooling air generated by the air circulation mechanism as will be discussed in detail below. Preferably, the channel 36 is connected to the target board 70 by means of a threaded fastener. However, it will be recognized by those of skill in the art that any suitable fastener apparatus, material or device may be used.

The channel 36 includes a base 38 and a pair of oppositely disposed elongated sidewalls 40 extending from the base 38. Each sidewall 40 has an elongated receptacle 66 formed therein for receiving an edge 82 of the cover 80. A gasket is disposed between the cover 80 and the receptacle 66 to seal the channel 36 (as will be discussed in detail below). A chamber 90 is defined when the cover 80 is operatively connected to the channel 36 such that the cover edges 82 are received within the opposed elongated receptacles 66.

At least one first port 42 is disposed in one of the side walls 40 for operative connection with the first conduit in order to define the first passageway for the fluid from the fluid source to the chamber. It is within the teachings of the present invention that each at least one first port 42 may also be disposed in either end wall 41. Each first port 42 is preferably configured as a threaded barb fitting for ease of assembly and interchangeability with a complementary threaded bore defined in the one of the side walls 40. It will be recognized by those of skill in the art that ports having different configurations and other suitable apparatus may be substituted therefor. For example, AN fittings, threaded pipe fittings, compression fittings, push-lock fittings or any other suitable apparatus. Moreover, the first ports 42 may be integrally formed as part of the side wall 40.

In one embodiment of the present invention, at least one second port 43 is disposed in one of the side walls 40 and is operatively connected to the second conduit to define the second passageway for removing the fluid from the chamber 90 at a desired rate. Preferably, each at least one second port 43 is disposed in opposition to the wall connected to the first ports 42, whether that is a side wall 40 or an end wall 41. It is within the teachings of the present invention that each second port 43 may be configured the same as taught for each first port 42 above.

The cover 80 is light transmittant and preferably includes a filter element. It is within the teachings of the present invention that the cover 80 and filter element may be integrally or independently formed. Preferably, the cover is transparent and the filter element is formed from borosilicate. It will be recognized by those of skill in the art that other constructions and configurations for the cover and filter element will provide suitable function. For example, the cover may also be translucent, formed of glass, or any other suitable material. The filter element may be formed from quartz, transparent substrate, translucent substrate, automobile window glass, architectural window glass, evaporated thin film optical coatings, interference filters, quarter-wave filters, specific wavelength-filtering elements, or any other suitable construction or configuration.

Figure 3:
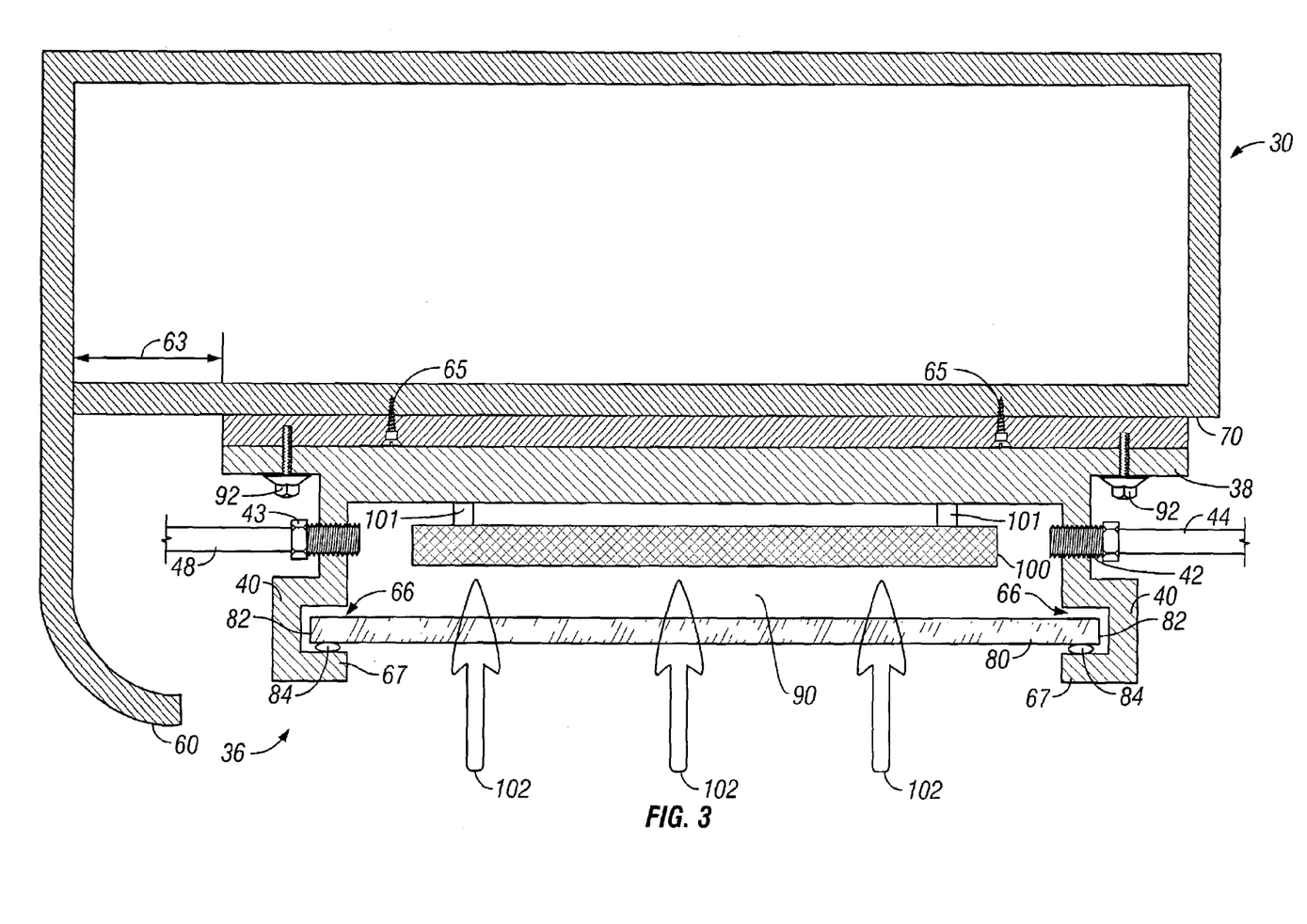
FIG. 3 is a cross-sectional view of the ONAWTA of FIG. 2 taken along line I—I.

FIG. 3 is a cross-sectional view of the exploded view of FIG. 2 taken along line I—I. The air tunnel 30 includes a support strut 64 and an air deflector 60. It will be recognized that this cross-sectional view is taken through the support strut 64 in order to illustrate how the target board 70 is connected to the air tunnel 30. A gap 63 is defined between the target board 70 and the wall of the air tunnel 30 adjacent the air deflector 60. The gap 63 is open to permit discharge of air therethrough. As discussed above, threaded fasteners 65 or any other suitable apparatus connect the target board 70 to the support strut 64.

The channel 36 is connected to the target board by way of threaded fasteners 92 as discussed above. The channel 36 includes a cover 80 to define a chamber 90 wherein a test specimen 100 is disposed therein for exposure to concentrated sunlight and ultraviolet radiation signified by the large arrows 102. The channel 36 further includes a base 38 and a pair of oppositely disposed, elongated sidewalls 40 extending from the base 38. Preferably, each sidewall 40 has an elongated receptacle 66 formed therein for receiving an edge 82 of the cover 80. A gasket 84 is disposed between the cover 80 and the receptacle 66 to seal the channel 36 such that fluid is retained within the chamber 90. A portion 67 of the receptacle 66 is so disposed to shield the gasket 84 from exposure to concentrated solar radiation 102. The service life of the gasket 84 is thereby increased significantly as are the accuracy and reproducibility of degradation test results.

It is within the teaching of the present invention that the receptacle 66 is not required to mount the cover 80 and shield the gasket 84. For example, the gasket 84 may be disposed atop each sidewall 40 with the cover 80 disposed thereon. A holder, such as a right angle element, may be configured to engage the cover 80 and the sidewall 40 in order to secure the cover 80 to the channel and shield the gasket 84 from exposure to concentrated solar radiation 102. Alternatively, the cover 80 may include an opaque element which shields the gasket 84 from exposure to concentrated solar radiation 102 when the receptacle or holder are not required for mounting the cover 80.

At least one first port 42 is disposed in one of the sidewalls 40 and a first conduit 44 operatively connects each at least one first port 42 to the fluid source (as discussed in FIGS. 4–7) such that the first conduit 44 and each at least one first port 44 defines the first passageway for the fluid from the fluid source to the chamber 90. At least one regulator is operatively connected to the first passageway for controlling the desired rate and amount of fluid introduced into the chamber 90.

At least one second port 43 is disposed in the other sidewall 40 and is operatively connected to a second conduit 48 to define a second passageway for removing the fluid from the chamber 90 at a desired rate. At least one regulator is operatively connected to the second passageway for controlling the desired rate of removing the fluid from the chamber 90.

The fluid removed from the chamber 90 is preferably analyzed for degradation products from the specimen 100. The analysis technique for identifying the degradation products from the specimen 90 may be any conventionally available process. For example, Fourier-transform infrared spectroscopy, gas chromatography, high-pressure liquid chromatography and any other suitable process may be used.

The specimen 100 may be mounted to the base 38 of the channel 36 or may preferably be offset from the base 38 a desired amount by stand-offs 101.

Figure 4:
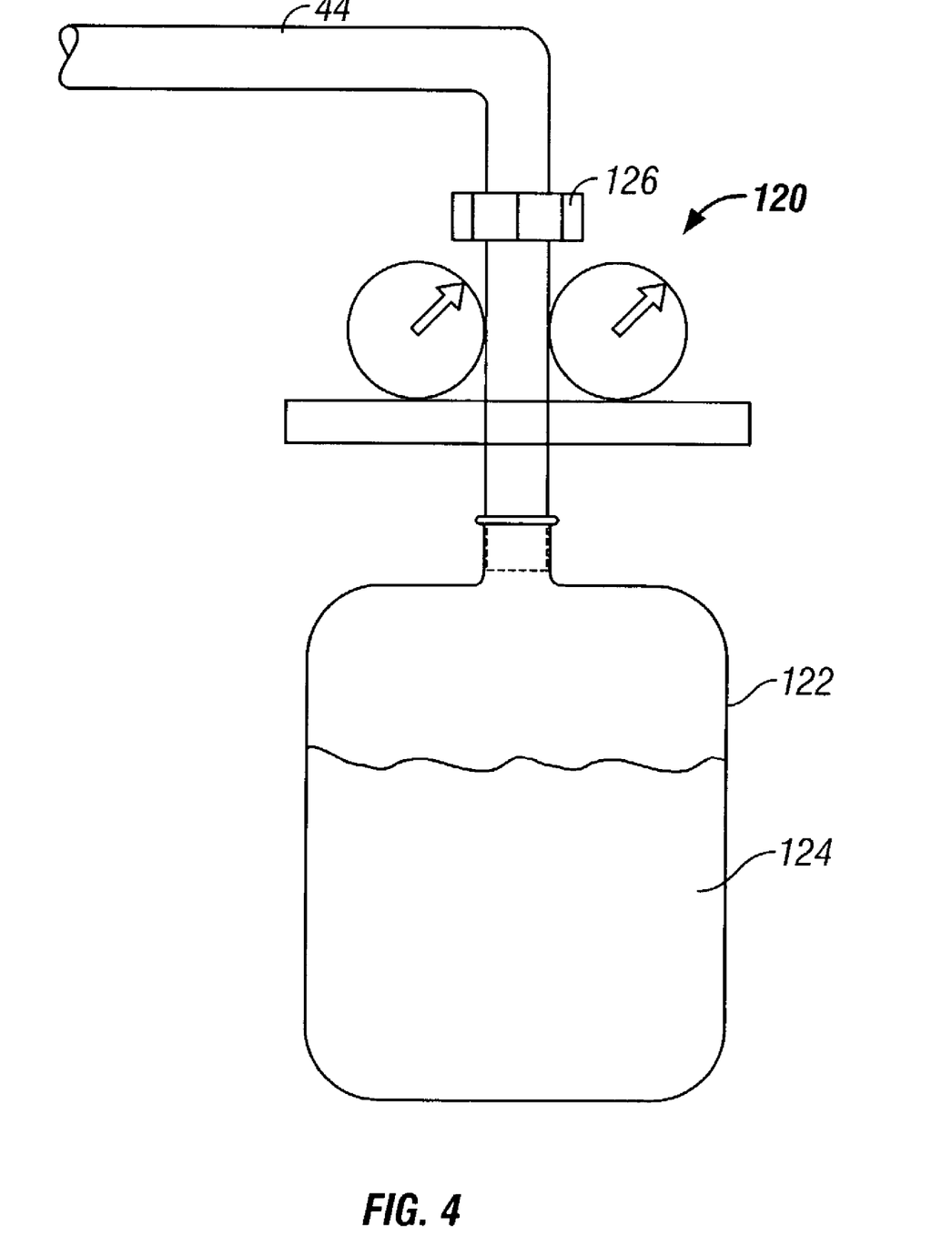
FIG. 4 is a schematic view of a fluid source operatively connected to the ONAWTA of FIG. 1.

FIG. 4 illustrates one embodiment of a fluid source 120 in accordance with the present invention. In this embodiment, the fluid source 120 includes a tank 122 containing the fluid 124 and a regulator 126 for controlling flow of the fluid 124 from the tank 122 to the chamber via the first passageway. The fluid 124 may be any suitable composition for enhancing degradation of the specimen. For example, the fluid may be water, oxygen, nitrogen, organic or inorganic solvents, acids, bases, salts, dissolved salts, oxides of sulfur, oxides of nitrogen, oxides of hydrogen, peroxides, ozone, or any other suitable fluid. Preferably, in this embodiment, the fluid 124 is a gas under pressure such that opening the regulator 126 enables flow of the fluid 124 to the chamber. The gas may be any gas suitable for enhancing degradation of the specimen. For example, the gas may be oxygen, nitrogen, oxides of sulfur, oxides of nitrogen, oxides of hydrogen, ozone, or any other suitable gas.

Figure 5:
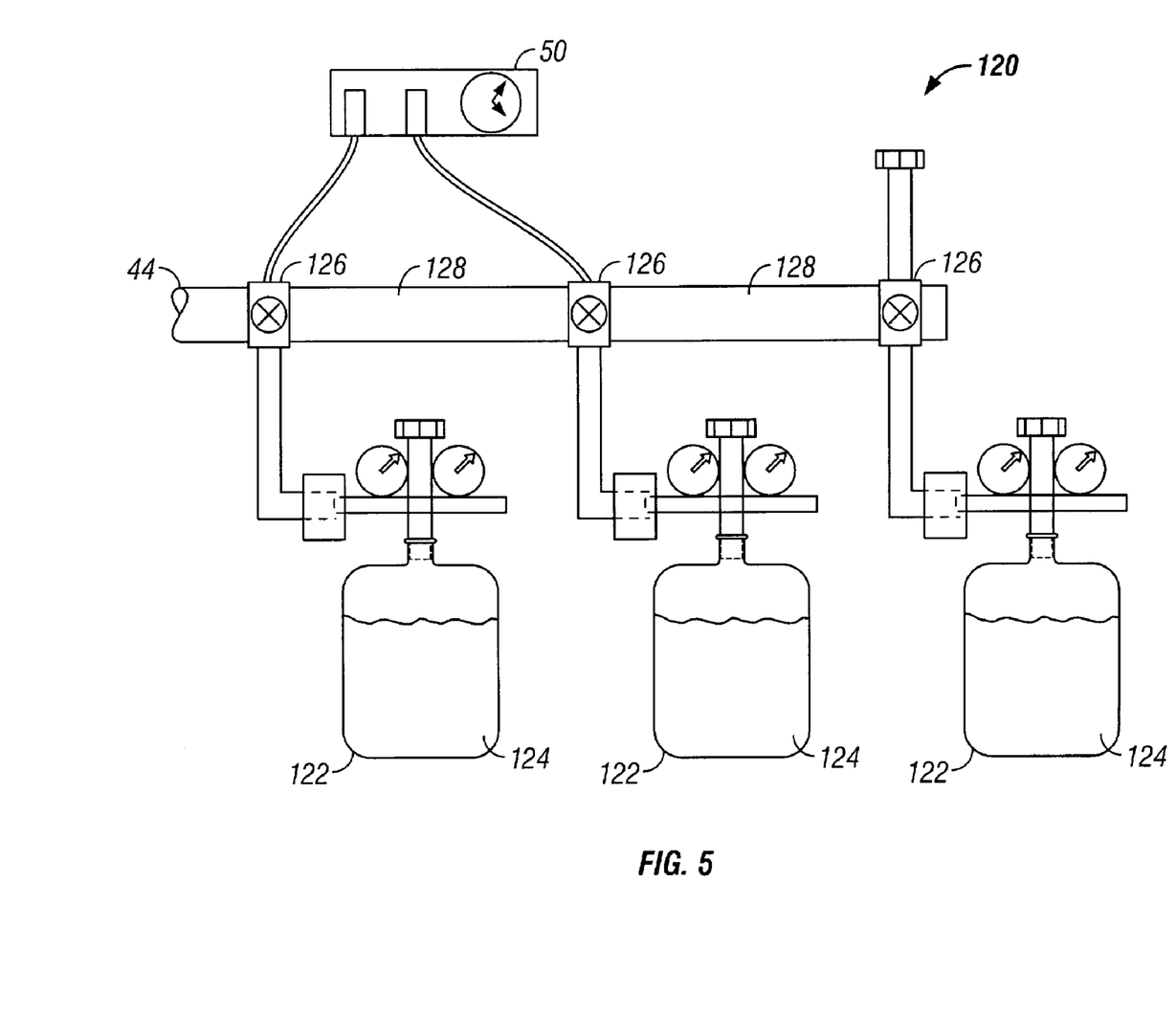
FIG. 5 is a schematic view of a fluid source operatively connected to the ONAWTA of FIG. 1.

FIG. 5 shows another embodiment of the fluid source 120 in accordance with the present invention. In this embodiment, the fluid source 120 includes a plurality of tanks 122, each holding a different fluid 124 and each operatively connected to a manifold 128 for communication via the first passageway with the chamber. A regulator 126 operatively connects each tank to the manifold 128 and at least one regulator 126 is electrically actuated by the control system 50. The fluid 124 disposed in each of the tanks 122 may be any suitable fluid for enhancing degradation of the specimen as discussed above. It is within the teachings of the present invention that one, more than one or all of the regulators 126 may be manually actuated.

Figure 6:
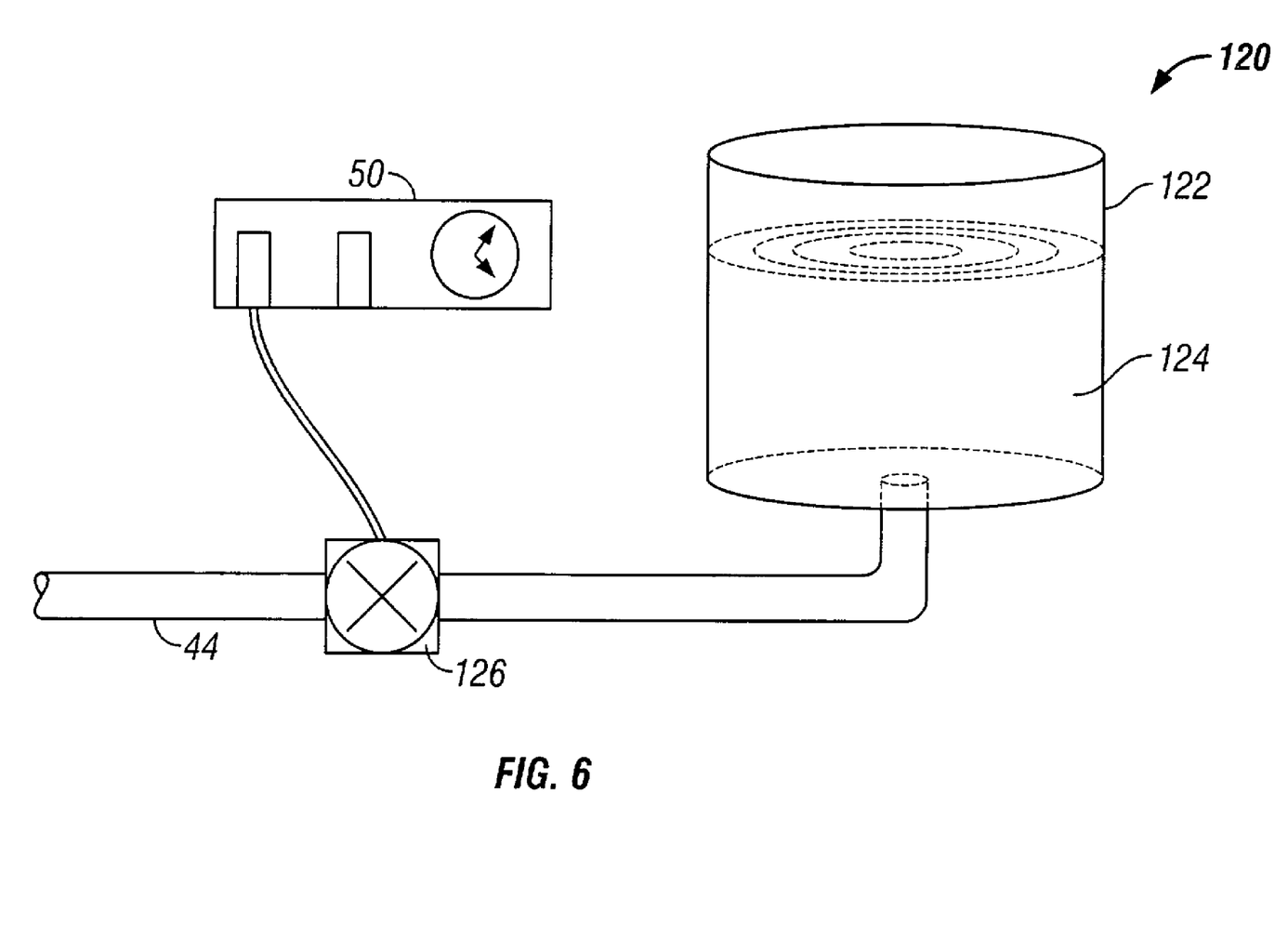
FIG. 6 is a schematic view of a fluid source operatively connected to the ONAWTA of FIG. 1.

FIG. 6 shows yet another embodiment of the fluid source 120 in accordance with the present invention. The fluid source 120, in this embodiment, includes a tank 122 containing fluid 124 and a regulator 126 for controlling flow of the fluid 124 from the tank 122 to the chamber via the first passageway. In this embodiment, the fluid 124 is preferably a liquid which may be any liquid suitable for enhancing degradation of the specimen. For example, the liquid may be water, organic and/or inorganic solvents, acids, bases, salts, dissolved salts, peroxides, or any other suitable liquid. In this embodiment, the control system 50 electrically actuates the regulator 126 to control flow of the fluid 124 from the tank 122 to the chamber. A pump may be operatively connected to the first passageway in order to enable the fluid 124 to flow from the tank 122 to the chamber. Other methods, such as gravity feed may also be used to provide identical functionality.

Figure 7:
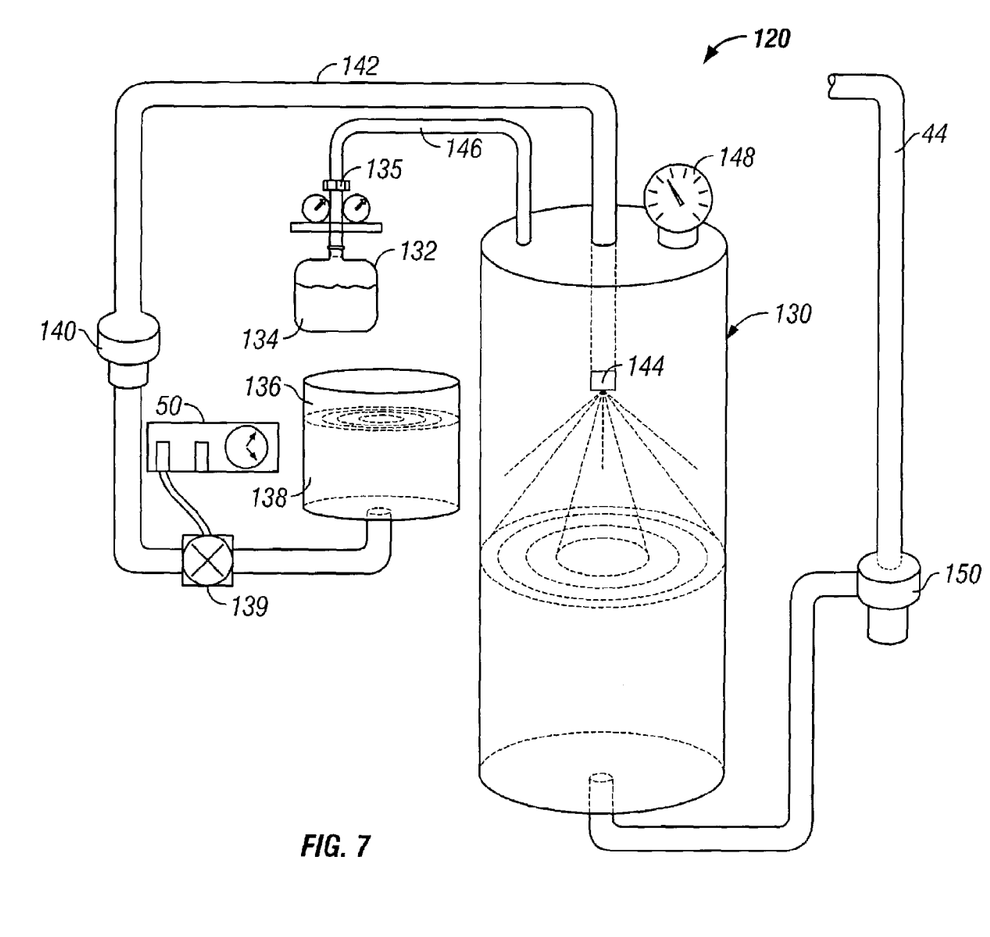
FIG. 7 is a schematic view of a fluid source operatively connected to the ONAWTA of FIG. 1.

FIG. 7 shows still another embodiment of the fluid source 120 in accordance with the present invention. The fluid source 120 in this embodiment includes an accumulator 130 in communication with a first tank 132, a second tank 136 and the chamber via the first passageway. The first tank 132 contains a gas 134 under pressure and has a regulator 135 for controlling flow of the gas 134 from the first tank 132 to the accumulator 130. The second tank 136 contains a liquid 138. It has a regulator 139 for controlling flow of the liquid 138 from the second tank 136 to the accumulator 130.

The liquid 138 is drawn from the second tank 136 through the regulator 139 by pump 140 which pumps the liquid through a conduit 142 into the accumulator 130. A nozzle 144 is disposed at the distal end of the conduit 142 in order to atomize and spray the liquid into the accumulator 130. The gas 134 in the first tank 132 is pressurized such that when the regulator 135 is opened, the gas 134 flows through conduit 146 and pressurizes the accumulator 130. The pressure in the accumulator is observable by a pressure gauge 148.

The accumulator 130 is pressurized such that the gas 134 diffuses into the liquid as it is sprayed into the accumulator 130. A pump 150 draws the gas/liquid 134, 138 combination from the accumulator 130 and directs such combination to the chamber via the first passageway. In this embodiment, the gas 134 may be any gas suitable for accelerating degradation of the test specimen. For example, the gas may be oxygen, nitrogen, oxides of sulfur, oxides of nitrogen, oxides of hydrogen, ozone, or any other suitable gas. Further, the liquid may be any liquid suitable for accelerating degradation of the test specimens. For example, the liquid may be water, organic solvents, inorganic solvents, acids, basis, salts, dissolved salts, peroxide or any other suitable liquid. The control system 50 electrically actuates at least one of the regulators. As shown in this embodiment, the liquid regulator 139 is electrically actuated by the control system 50 and the gas regulator 135 is manually controlled. It will be recognized that the control system may electrically actuate both regulators if so desired in order to achieve the intended function.

Figure 8:
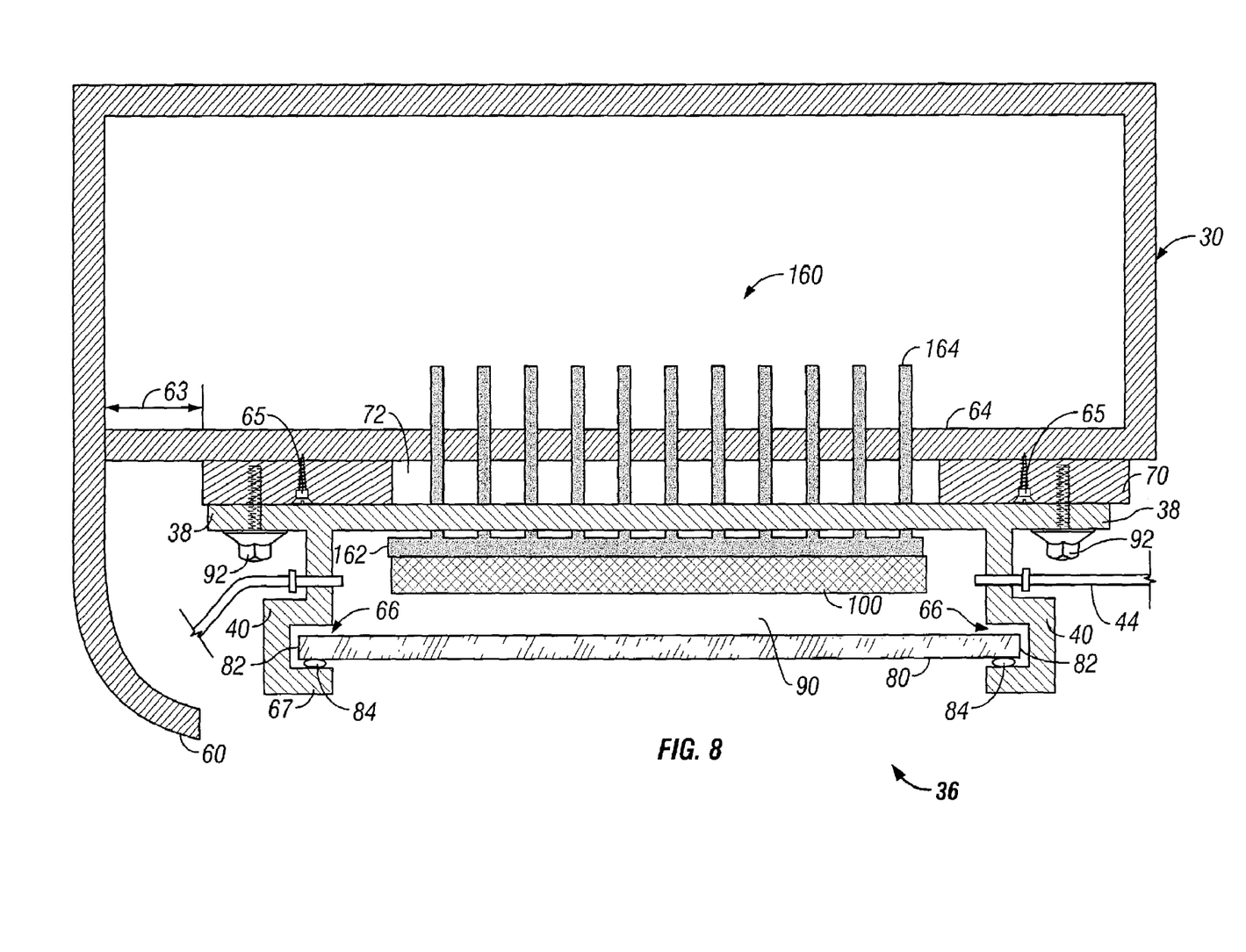
FIG. 8 is a cross-sectional view of another embodiment of the ONAWTA of FIG. 2 taken along line I—I.

FIG. 8 shows another embodiment of the present invention. In this embodiment, the air tunnel 30 is in communication with a fan for moving air therethrough in order to maintain the test specimens at a desired temperature in a manner which will be described in detail below. The volume of air moved by the fan is adjusted by the control system in a conventional manner as described in U.S. Pat. No. 4,807,247 issued to Robbins, III, incorporated fully herein by reference or any other suitable control system.

The air tunnel 30 includes a support strut 64 and an air deflector 60. It will be recognized that this cross sectional view is taken through the support strut 64 in order to demonstrate how the target board 70 is connected to the air tunnel 30 and that the gap 63 defined between the target board and the wall of the air tunnel 30 adjacent the air deflector 60 is open to permit discharge of air therethrough which is particularly important in this embodiment. As discussed above, threaded fasteners 65 preferably connect the target board 70 to the support strut 64.

The target board 70, in this embodiment, is configured as generally described above and further includes a plurality of openings 72 formed therein in order to facilitate maintaining the specimen 100 at a desired temperature as will be discussed in detail below.

The channel 36 is connected to the target board 70 by threaded fasteners 92 as discussed above. The channel 36 further includes a cover 80 to define a chamber 90 wherein the test specimen 100 is disposed for exposure to ultraviolet radiation from the reflecting solar concentrator. The channel 36 further includes a base 38 and a pair of oppositely disposed elongated sidewalls 40 extending from the base 38. Each sidewall 40 has an elongated receptacle 66 formed therein for receiving an edge 82 of the cover 80.

A gasket 84 is disposed between the cover 80 and the receptacle 66 to seal the channel 36 such that fluid is retained within the chamber 90. Pressure exerted by the fluid on the cover 80 forces the cover 80 against the gasket 84 to provide the appropriate seal. A portion 67 of the sidewall 40 shields the gasket 84 from exposure to concentrated solar radiation from the reflecting solar concentrator. It is within the teachings of the present invention that the gasket may be formed of any suitable material. For example, the gasket may be formed of rubber, silicone, neoprene, nylon or any other engineered or natural elastomeric material.

An apparatus 160 is disposed contiguous with one side of the specimen 100 and maintains a specimen at a desired temperature. The apparatus 160 includes a base 162 contiguous with the specimen and at least one fin 164 which extends from the base 162 through the base 38 of the channel 36 and the opening 72 of the target board 70 into the air tunnel 30. The at least one fin 164 transfers and dissipates heat from the specimen 100 to the air moving through the air tunnel 30 by the fan. The air is then discharged through the gap past the air deflector 60. In this embodiment, the apparatus 160 is preferably a metallic heat sink. It will be recognized that the apparatus may also be structurally configured from any other material having suitable heat transfer properties. For example, the apparatus may be constructed of any non-insulative material capable of conducting heat.

At least one first port 42 is disposed in one of the sidewalls 40 and a first conduit 44 operatively connects each at least one first port 42 to the fluid source (as discussed in FIGS. 4–7) such that the first conduit 44 and each at least one first port 44 defines the first passageway for the fluid from the fluid source to the chamber 90. Each at least one first port may be configured and constructed as described above. At least one regulator is operatively connected to the first passageway for controlling the desired rate of fluid supply.

In one embodiment of the present invention, at least one second port 43 is disposed in the other sidewall 40 and is operatively connected to a second conduit 48 to define a second passageway for removing the fluid from the chamber 90 at a desired rate. Each at least one second port may be configured and constructed as described above. Further, alternative embodiments for supply and removal of the fluid from the chamber may be provided. For example, in addition to the embodiments described above, the first conduit and the second or third conduit as the case may be are concentric. At least one regulator is operatively connected to the second passageway for controlling the desired rate of removing the fluid.

The fluid removed from the chamber 90 may be analyzed for degradation products from the specimen 100. The analysis technique for identifying the degradation products from the specimen 90 may be any conventionally available process. For example, Fourier-transformed infrared spectroscopy, gas chromatography, high-pressure liquid chromatography and any other suitable process may be used.

It will be recognized that the first port 42 in this embodiment is configured as a push fit or interference fitting which does not require threads to engage the sidewall 40 of the channel 36. Other various configurations for providing a port have been discussed above. The first conduit 44 may be connected to the port 42 in any conventional manner, such as circumferential gripping, hose barbs, hose clamp compression, or any other suitable connecting configuration.

Other structural and functional aspects of this embodiment of the present invention are identical to embodiments that described above.

Figure 9:
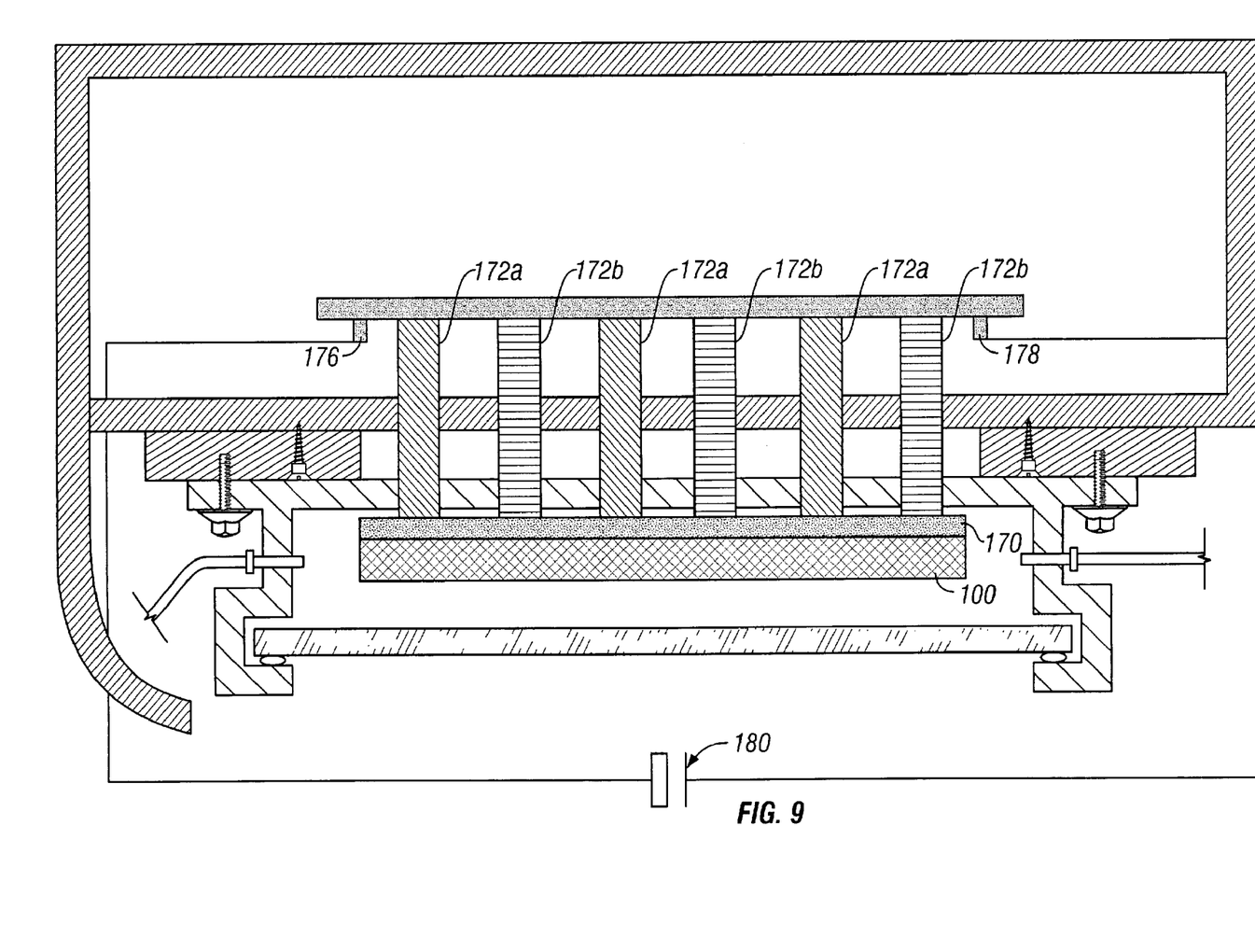
FIG. 9 is another alternative embodiment of the ONAWTA of FIG. 2 taken along line I—I.

FIG. 9 shows a cross-sectional view of yet another embodiment in accordance with the present invention. The general structure and function of this embodiment is as described above with respect to FIGS. 3 and 8. However, the apparatus 160 in this embodiment is configured differently to provide the same function. In this embodiment, the apparatus 160 includes a base 170 contiguous with the specimen 100. At least two spaced legs 172a, 172b extend from the base 170 into the air tunnel 30 in order to dissipate heat from the specimen 100 to the air moving through the air tunnel 30. A top 174 is connected to the legs 172a, 172b and has a first end 176 and a second end 178 to which a voltage source 180 is applied. Preferably, the apparatus 160 is a thermoelectric apparatus having legs constructed of semiconductor material such that the voltage differential between the first end 176 and second end 178 results in dissipation of heat from the specimen 100 to the air moving through the air tunnel 30.

It will be recognized that the thermoelectric apparatus is a solid state heat pump that operates on the Peltier effect, the theory that there is a heating or cooling effect when electric current passes through two conductors. A voltage applied to the free ends of two dissimilar materials creates a temperature difference. With this temperature difference, Peltier cooling will cause heat to move from one end to the other. In this embodiment, the thermoelectric apparatus consists of an array of p- and n-type semiconductor elements that act as two dissimilar conductors. Namely, leg 172a is a p-type while leg 172b is an n-type semi-conductor element. In the event other legs are used, as shown, the array repeats in succession p-type, n-type, p-type, n-type. The array of elements is soldered between two ceramic plates, electrically in series and thermally in parallel. As a DC current passes through one or more pairs of elements from n-type to p-type, there is a decrease in temperature at the base 170 (cold side) resulting in the absorption of heat from the test specimen 100. The heat is carried through the thermal electric apparatus by electron transport and released on the top 174 (hot side) as the electrons move from a high to low energy state. The heat pumping capacity of a thermoelectric apparatus 160 is proportional to the current and the number of pairs of n-type and p-type elements (or couples) in the apparatus. The air circulation mechanism moves air through the legs of the thermoelectric apparatus whereby heat is transferred from the top 179 to the air which is then discharged through the gap and past the air deflector.

The remaining structure and function of this embodiment of the present invention is the same as described above in connection with FIGS. 3 and 8.

Figure 10:
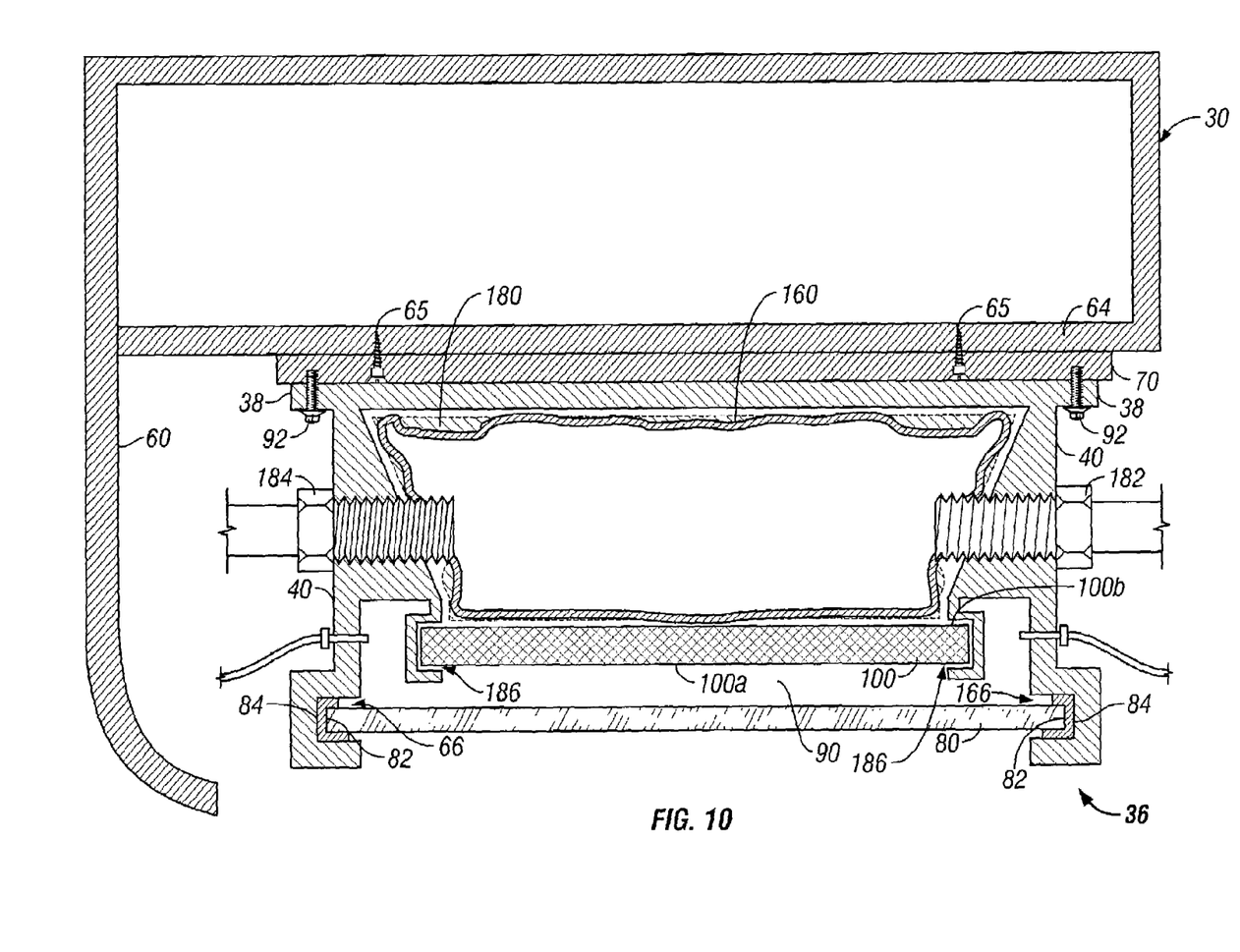
FIG. 10 is another alternative embodiment of the ONAWTA of FIG. 2 taken along line I—I.

FIG. 10 is a cross-sectional view of still another embodiment of the present invention directed to an accelerated weathering apparatus of the type used to concentrate solar radiation upon test specimens 100. It will be recognized that his embodiment of the present invention is similar to the embodiment described in FIG. 3. The air tunnel 30 includes a support strut 64 and an air deflector 60. However, as with the embodiment described in FIG. 3, the air circulation mechanism is not required for this embodiment to properly function. As discussed above, the target board 70 is connected to the support strut 64 with appropriate fasteners as described above.

The channel 36 is connected to the target board 70 by way of threaded fasteners 92 or other suitable fasteners, as discussed above. The channel 36 includes a cover 80 to define a chamber 90. The channel 36 further includes a base 38 and a pair of oppositely disposed, elongated sidewalls 40 extending from the base 38. Each sidewall 40 has an elongated receptacle 66 formed therein for receiving an edge 82 of the cover 80. A gasket 84 is disposed between the cover 80 and the receptacle 66 to seal the channel 36 such that fluid is retained within the chamber 90. Preferably, in this embodiment, the gasket 84 is C-shaped in order to receive the edge 82 of the cover 80 therein and conform to each surface which defines the receptacle 66. As a result, the gasket 84 in this embodiment does not rely upon the pressure of the fluid in order to seal the chamber 90.

A specimen 100 is disposed within the chamber 90 to define a cavity 180 such that a first side 100a of the specimen 100 is exposed to the chamber 90 and a second side 100b of the specimen 100 is exposed to the cavity 180. A apparatus 160 is disposed within the cavity 180 contiguous with the specimen 100 for maintain the specimen 100 at a desired temperature.

In this embodiment, the apparatus 160 is configured as a flexible walled vessel for receiving a coolant to maintain the specimen at a desired temperature. The flexible walled vessel 160 as shown in FIG. 10 in solid, is disposed in a first operative position wherein there is no coolant disposed within the flexible walled vessel 160. In a second operative position, as shown in FIG. 10 in phantom, the flexible walled vessel 160 has coolant disposed therein and therefor expands to conform to the specimen and cavity walls.

The flexible walled vessel 160 is operatively connected to an inlet 182 which is in communication with a coolant source and an outlet 184 which is regulated to remove the coolant from the flexible walled vessel at a desired rate. The coolant and flexible walled vessel, in this embodiment, may be constructed of any non-insulative material suitable for absorbing heat from the specimen 100. For example, the coolant may be refrigerated air, ethylene glycol, fluorocarbon refrigerants, alcohol, refrigerant gases, fluids used for heat exchange or any other suitable material. The flexible walled vessel may be constructed of any natural or engineered elastomeric material, such as rubber, or any other suitable material.

It will be recognized from FIG. 10 that the specimen 100 is disposed relatively loosely within grooves 186 formed in the chamber. This configuration aids removal and replacement of the specimen 100. However, it will be recognized that these specimens 100 may also be removably attached in any suitable manner to the grooves 186 or other mounting structure as provided and achieve the same function described herein.

The coolant source may be configured in accordance with any embodiment discussed above with regard to FIGS. 4–7 in order to achieve the desired cooling effect. In other words, the coolant source may have a tank, plurality of tanks, combination of gases and liquids, and accumulator for combining the gas and liquid, electrically actuated regulators, pumps or any other structural or functional configuration described above with respect to FIGS. 4–7.

This embodiment of the present invention further includes at least one first port 42, at least one second port 43, fluid source, cover and any and all other structural elements as described above in detail with respect to FIG. 3 in order to achieve the functionality described above.

While the invention has been described with reference to a preferred embodiment thereof, the description is for illustrative purposes only and is not to be construed as limiting the scope of the invention. Various modifications and changes may be made by those skilled in the art without departing from the true spirit and scope of the invention as defined by the dependent claims. For example, mechanical or optical control apparatus may be substituted for the control and input signals and that other methods to effect temperature using the mirrors rather than the blown air may be used. For instance, defocusing mirrors instead of changing the blowers speed may provide the same results. Additionally, a damper or mechanical valve in the air tunnel may be used to change the amount of cooling air circulated over the test specimen. Finally, filters (polarizing, interference, tunable, etc.) may be used to effect the radiance and the temperature.

What is claimed is:

1. An accelerated weathering apparatus of the type used to concentrate solar radiation upon test specimens including a frame supporting a reflecting solar concentrator disposed in opposition to a target board, said accelerated weathering apparatus comprising:
a channel connected to the target board including a cover to define a chamber; and
a fluid source in communication with the chamber whereby a fluid introduced into the chamber reacts with the specimen in order to accelerate degradation of the specimen during exposure to concentrated solar radiation.

2. The apparatus recited by claim 1, wherein the channel further includes a base and a pair of oppositely disposed, elongated sidewalls extending from the base.

3. The apparatus recited by claim 2, wherein each sidewall has an elongated receptacle formed therein for receiving an edge of the cover.

4. The apparatus recited by claim 3, wherein a gasket is disposed between the cover and the receptacle to seal the channel such that the fluid is retained within the chamber.

5. The apparatus recited in claim 4, wherein a portion of the receptacle shields the gasket from exposure to concentrated solar radiation.

6. The apparatus recited by claim 2, wherein at least one first port is disposed in one of the sidewalls and a first conduit operatively connects each at least one first port to the fluid source, such that the first conduit and each at least one first port defines a first passageway for the fluid from the fluid source to the chamber.

7. The apparatus recited by claim 6, wherein a second port is disposed in the other of the sidewalls and is operatively connected to a second conduit which defines a second passageway for removing the fluid from the chamber at a desired rate.

8. The apparatus recited by claim 7, wherein a regulator is operatively connected to the second passageway for controlling the desired rate removing the fluid.

9. The apparatus recited by claim 8, wherein the fluid removed from the chamber is analyzed for degradation products from the specimen.

10. The apparatus recited by claim 9, wherein the analysis is selected from a group of analysis techniques consisting essentially of Fourier transform infrared spectroscopy, gas chromatography and high pressure liquid chromatography.

11. The apparatus recited by claim 6, wherein a regulator is operatively connected to the first passageway and a third conduit such that the regulator may be actuated to remove the fluid from the chamber through the third conduit.

12. The apparatus recited by claim 1, wherein the fluid is selected from a group consisting essentially of water, oxygen, nitrogen, organic and inorganic solvents, acids, bases, salts, dissolved salts, oxides of sulfur, oxides of nitrogen, oxides of hydrogen, peroxides and ozone.

13. The apparatus recited by claim 1, wherein the cover is light transmittant and includes a filter element.

14. The apparatus recited by claim 13, wherein the filter element is selected from a group consisting essentially of borosilicate, quartz, transparent substrate, translucent substrate, automobile window glass, architectural window glass, evaporated thin film optical coatings, interference filters, quarter wave filters and specific wave length filtering elements.

15. The apparatus recited by claim 1, wherein the fluid source includes a tank containing the fluid and a regulator for controlling flow of the fluid from the tank to the chamber.

16. The apparatus recited by claim 15, wherein the apparatus further includes a control system which electrically actuates the regulator whereby the fluid flows to the chamber.

17. The apparatus recited by claim 15, wherein the fluid is selected from a group consisting essentially of water, oxygen, nitrogen, organic and inorganic solvents, acids, bases, salts, dissolved salts, oxides of sulfur, oxides of nitrogen, oxides of hydrogen, peroxides and ozone.

18. The apparatus recited by claim 1, wherein the fluid source includes a plurality of tanks each holding a different fluid operatively connected to a manifold for communication with the chamber.

19. The apparatus recited by claim 18, wherein a regulator operatively connects each tank to the manifold and the apparatus further includes a control system which electrically actuates at least one regulator.

20. The apparatus recited by claim 18, wherein the fluid is selected from a group consisting essentially of water, oxygen, nitrogen, organic and inorganic solvents, acids, bases, salts, dissolved salts, oxides of sulfur, oxides of nitrogen, oxides of hydrogen, peroxides and ozone.

21. The apparatus recited by claim 1, wherein the fluid source includes an accumulator in communication with a first tank, a second tank and the chamber, the first tank containing a gas under pressure having a regulator for controlling flow of the gas from the first tank to the accumulator, the second tank containing a liquid having a regulator for controlling flow of the liquid from the second tank to the accumulator, wherein the liquid is sprayed into the accumulator by a nozzle and the gas pressurizes the accumulator such that the gas diffuses into the sprayed liquid before the fluid is pumped into the chamber.

22. The apparatus recited by claim 21, wherein the gas is selected from a group consisting essentially of oxygen, nitrogen, oxides of sulfur, oxides of nitrogen, oxides of hydrogen and ozone.

23. The apparatus recited by claim 21, wherein the liquid is selected from a group consisting essentially of water, organic and inorganic solvents, acids, bases, salts, dissolved salts and peroxides.

24. The apparatus recited by claim 21, wherein the apparatus further includes a control system which electrically actuates at least one of the regulators.

25. The apparatus as recited by claim 1, wherein a gasket is disposed between the channel and the cover such that the gasket is shielded from concentrated solar radiation.

26. An accelerated weathering apparatus of the type used to concentrate solar radiation upon test specimens including a frame supporting a reflecting solar concentrator disposed in opposition to an air tunnel having a fan for moving air therethrough and a target board, said accelerated weathering apparatus comprising:
a channel connected to the target board including a cover to define a chamber;

a specimen disposed within the chamber; and an apparatus contiguous with the specimen for maintaining the specimen at a desired temperature.

27. The apparatus recited by claim 26, wherein the apparatus includes a base contiguous with the specimen and at least one fin which extends from the base into the air tunnel in order to dissipate heat from the specimen to air moved through the air tunnel by the fan.

28. The apparatus recited by claim 27, wherein the apparatus is a metallic heat sink.

29. The apparatus recited by claim 26, wherein the apparatus includes a base contiguous with the specimen, at least two legs which extend from the base into the air tunnel in order to dissipate heat from the specimen to the air moving through the air tunnel, a top connected to each leg having a first end and a second end and a voltage source applied across the first and second ends of the top.

30. The apparatus recited by claim 28, wherein adjacent legs are constructed of dissimilar semiconductor material.

31. The apparatus recited by claim 26, further including a fluid source in communication with the chamber whereby a fluid introduced into the chamber reacts with the specimen in order to accelerate degradation of the specimen during exposure to concentrated solar radiation.

32. The apparatus recited by claim 26, wherein the channel further includes a base and a pair of oppositely disposed, elongated sidewalls extending from the base.

33. The apparatus recited by claim 32, wherein each sidewall has an elongated receptacle formed therein for receiving an edge of the cover.

34. The apparatus recited by claim 33, wherein a gasket is disposed between the cover and the receptacle to seal the channel such that the fluid is retained within the chamber.

35. The apparatus recited in claim 34, wherein a portion of the receptacle shields the gasket from exposure to concentrated solar radiation.

36. The apparatus recited by claim 32, wherein at least one first port is disposed in one of the sidewalls and a first conduit operatively connects each at least one first port to the fluid source, such that the conduit and each at least one first port defines a first passageway for the fluid from the fluid source to the chamber.

37. The apparatus recited by claim 36, wherein a second port is disposed in the other of the sidewalls and is operatively connected to a second conduit which defines a second passageway for removing the fluid from the chamber at a desired rate.

38. The apparatus recited in claim 37, wherein a regulator is operatively connected to the second passageway for controlling the desired rate of fluid removal.

39. The apparatus recited by claim 38, wherein the fluid removed from the chamber is analyzed for degradation products from the specimen.

40. The apparatus recited by claim 39, wherein the analysis is selected from a group of analysis techniques consisting essentially of Fourier transform infrared spectroscopy, gas chromatography and high pressure liquid chromatography.

41. The apparatus by claim 36, wherein a regulator is operatively connected to the first passageway and a third conduit such that the regulator may be actuated to remove the fluid from the chamber through the third conduit.

42. The apparatus recited by claim 26, wherein the fluid is selected from a group consisting essentially of water, oxygen, nitrogen, organic and inorganic solvents, acids, bases, salts, dissolved salts, oxides of sulfur, oxides of nitrogen, oxides of hydrogen, peroxides and ozone.

43. The apparatus recited by claim 26, wherein the cover is light transmittant and includes a filter element.

44. The apparatus recited by claim 43, wherein the filter element is selected from a group consisting essentially of borosilicate, quartz, transparent substrate, translucent substrate, automobile window glass, architectural window glass, evaporated thin film optical coatings, interference filters, quarter wave filters and specific wave length filtering elements.

45. The apparatus recited by claim 26, wherein the fluid source includes a tank containing the fluid and a regulator for controlling flow of the fluid from the tank to the chamber.

46. The apparatus recited by claim 45, wherein the apparatus further includes a control system which electrically actuates the regulator whereby the fluid is conveyed to the chamber.

47. The apparatus recited by claim 45, wherein the fluid is selected from a group consisting essentially of water, oxygen, nitrogen, organic and inorganic solvents, acids, bases, salts, dissolved salts, oxides of sulfur, oxides of nitrogen, oxides of hydrogen, peroxides and ozone.

48. The apparatus recited by claim 26, wherein the fluid source includes a plurality of tanks each holding a different fluid operatively connected to a manifold for communication with the chamber.

49. The apparatus recited by claim 48, wherein a regulator operatively connects each tank to the manifold and the apparatus further includes a control system which electrically actuates at least one regulator.

50. The apparatus recited by claim 48, wherein the fluid is selected from a group consisting essentially of water, oxygen, nitrogen, organic and inorganic solvents, acids, bases, salts, dissolved salts, oxides of sulfur, oxides of nitrogen, oxides of hydrogen, peroxides and ozone.

51. The apparatus recited by claim 26, wherein the fluid source includes an accumulator in communication with a first tank, a second tank and the chamber, the first tank containing a gas under pressure having a regulator for controlling flow of the gas from the first tank to the accumulator, the second tank containing a liquid having a regulator for controlling flow of the liquid from the second tank to the accumulator, wherein the liquid is sprayed into the accumulator by a nozzle and the gas pressurizes the accumulator such that the gas diffuses into the sprayed liquid before the fluid is pumped into the chamber.

52. The apparatus recited by claim 51, wherein the gas is selected from a group consisting essentially of oxygen, nitrogen, oxides of sulfur, oxides of nitrogen, oxides of hydrogen and ozone.

53. The apparatus recited by claim 51, wherein the liquid is selected from a group consisting essentially of water, organic and inorganic solvents, acids, bases, salts, dissolved salts and peroxides.

54. The apparatus recited by claim 51, wherein the apparatus further includes a control system which electrically actuates at least one of the regulators.

55. The apparatus as recited by claim 26, wherein a gasket is disposed between the channel and the cover such that the gasket is shielded from concentrated solar radiation.

56. An accelerated weathering apparatus of the type used to concentrate solar radiation upon test specimens including a frame for supporting a reflecting solar concentrator disposed in opposition to a target board, said accelerated weathering apparatus comprising:

a channel connected to the target board including a cover to define a chamber;

a specimen disposed within the chamber to define a cavity such that a first side of the specimen is exposed to the chamber and a second side of the specimen is exposed to the cavity; and an apparatus disposed within the cavity contiguous with the specimen for maintaining the specimen at a desired temperature.

57. The apparatus recited by claim 56, wherein the apparatus includes a flexible walled vessel containing a coolant adequate to maintain the specimen at the desired temperature wherein the flexible walled vessel conforms to the specimen and cavity as a result of the coolant disposed therein.

58. The apparatus recited by claim 57, wherein the flexible walled vessel is operatively connected to an inlet in communication with a coolant source and an outlet regulated to remove the coolant from the flexible walled vessel at a desired rate.

59. The apparatus recited by claim 57, wherein the coolant is selected from the group consisting essentially of refrigerated air, ethylene glycol, fluorocarbon refrigerants, alcohol, refrigerant gases and fluids used for heat exchange.

60. The apparatus recited by claim 56, wherein the channel further includes a base and a pair of oppositely disposed, elongated sidewalls extending from the base.

61. The apparatus recited by claim 60, wherein each sidewall has an elongated receptacle formed therein for receiving an edge of the cover.

62. The apparatus recited by claim 61, wherein a gasket is disposed between the cover and the receptacle to seal the channel such that the fluid is retained within the chamber.

63. The apparatus recited in claim 62, wherein a portion of the receptacle shields the gasket from exposure to concentrated solar radiation.

64. The apparatus recited by claim 60, wherein at least one first port is disposed in one of the sidewalls and a first conduit operatively connects each at least one first port to the fluid source, such that the conduit and each at least one first port defines a first passageway for the fluid from the fluid source to the chamber.

65. The apparatus recited by claim 64, wherein a second port is disposed in the other of the sidewalls and is operatively connected to a second conduit which defines a second passageway for removing the fluid from the chamber at a desired rate.

66. The apparatus recited in claim 65, wherein a regulator is operatively connected to the second passageway for controlling the desired rate of fluid removal.

67. The apparatus recited by claim 66, wherein the fluid removed from the chamber is analyzed for degradation products from the specimens.

68. The apparatus recited by claim 67, wherein the analysis is selected from a group of analysis techniques consisting essentially of Fourier transform infrared spectroscopy, gas chromatography and high pressure liquid chromatography.

69. The apparatus by claim 64, wherein a regulator is operatively connected to the first passageway and a third conduit such that the regulator may be actuated to remove the fluid from the chamber through the third conduit.

70. The apparatus recited by claim 56, wherein the fluid is selected from a group consisting essentially of water, oxygen, nitrogen, organic and inorganic solvents, acids, bases, salts, dissolved salts, oxides of sulfur, oxides of nitrogen, oxides of hydrogen, peroxides and ozone.

71. The apparatus recited by claim 56, wherein the cover is light transmittant and includes a filter element.

72. The apparatus recited by claim 71, wherein the filter element is selected from a group consisting essentially of borosilicate, quartz, transparent substrate, translucent substrate, automobile window glass, architectural window glass, evaporated thin film optical coatings, interference filters, quarter wave filters and specific wave length filtering elements.

73. The apparatus recited by claim 56, wherein the fluid source includes a tank containing the fluid and a regulator for controlling flow of the fluid from the tank to the chamber.

74. The apparatus recited by claim 73, wherein the apparatus further includes a control system which electrically actuates the regulator whereby the fluid is conveyed to the chamber.

75. The apparatus recited by claim 73, wherein the fluid is selected from a group consisting essentially of water, oxygen, nitrogen, organic and inorganic solvents, acids, bases, salts, dissolved salts, oxides of sulfur, oxides of nitrogen, oxides of hydrogen, peroxides and ozone.

76. The apparatus recited by claim 56, wherein the fluid source includes a plurality of tanks each holding a different fluid operatively connected to a manifold for communication with the chamber.

77. The apparatus recited by claim 76, wherein a regulator operatively connects each tank to the manifold and the apparatus further includes a control system which electrically actuates at least one regulator.

78. The apparatus recited by claim 76, wherein the fluid is selected from a group consisting essentially of water, oxygen, nitrogen, organic and inorganic solvents, acids, bases, salts, dissolved salts, oxides of sulfur, oxides of nitrogen, oxides of hydrogen, peroxides and ozone.

79. The apparatus recited by claim 56, wherein the fluid source includes an accumulator in communication with a first tank, a second tank and the chamber, the first tank containing a gas under pressure having a regulator for controlling flow of the gas from the first tank to the accumulator, the second tank containing a liquid having a regulator for controlling flow of the liquid from the second tank to the accumulator, wherein the liquid is sprayed into the accumulator by a nozzle and the gas pressurizes the accumulator such that the gas diffuses into the sprayed liquid before the fluid is pumped into the chamber.

80. The apparatus recited by claim 79, wherein the gas is selected from a group consisting essentially of oxygen, nitrogen, oxides of sulfur, oxides of nitrogen, oxides of hydrogen and ozone.

81. The apparatus recited by claim 79, wherein the liquid is selected from a group consisting essentially of water, organic and inorganic solvents, acids, bases, salts, dissolved salts and peroxides.

82. The apparatus recited by claim 79, wherein the apparatus further includes a control system which electrically actuates at least one of the regulators.

83. The apparatus as recited by claim 56, wherein a gasket is disposed between the channel and the cover such that the gasket is shielded from concentrated solar radiation.

* * * * *